United States Patent [19]

Johansson et al.

[11] 3,988,112

[45] Oct. 26, 1976

[54] NOZZLE STERILIZER PROVIDING OUTER AND INNER ANNULAR CONCENTRIC COOLING JETS

[75] Inventors: Bjorn-Olow Johansson, Lomma; Bengt Arne Palm, Genarp, both of Sweden

[73] Assignee: Alfa-Laval AB, Tumba, Sweden

[22] Filed: Dec. 6, 1974

[21] Appl. No.: 530,418

Related U.S. Application Data

[62] Division of Ser. No. 404,622, Oct. 9, 1973, Pat. No. 3,927,974.

[52] U.S. Cl. .................................... 21/92; 21/56; 99/455; 239/417.3; 239/429
[51] Int. Cl.² .................. A23C 3/02; A23C 3/04; A61L 3/00; B05B 7/12
[58] Field of Search ......................... 21/92, 56, 91; 239/416.5, 417, 417.3, 423, 424.5, 429; 99/452, 455

[56] References Cited

UNITED STATES PATENTS

| | | | |
|---|---|---|---|
| 1,779,849 | 10/1930 | Lusk | 239/417.3 |
| 1,995,934 | 3/1935 | Mangold | 239/416.5 |
| 2,368,178 | 1/1945 | Turpin | 239/417 |
| 3,387,784 | 6/1968 | Ward | 239/424.5 |
| 3,610,537 | 10/1971 | Nakagawa et al. | 239/424.5 |

Primary Examiner—Norman Yudkoff
Assistant Examiner—Dale Lovercheck
Attorney, Agent, or Firm—Cyrus S. Hapgood

[57] ABSTRACT

Annular concentric jets of steam and a liquid to be sterilized, respectively, are contacted with each other in a jet nozzle; and the resulting annular jet of steam-heated liquid is swept along both its inside and its outside by two additional annular jets of cold liquid concentric to the first-mentioned jets, thereby preventing material from the liquid to be sterilized from burning onto surfaces of the jet nozzle.

4 Claims, 1 Drawing Figure

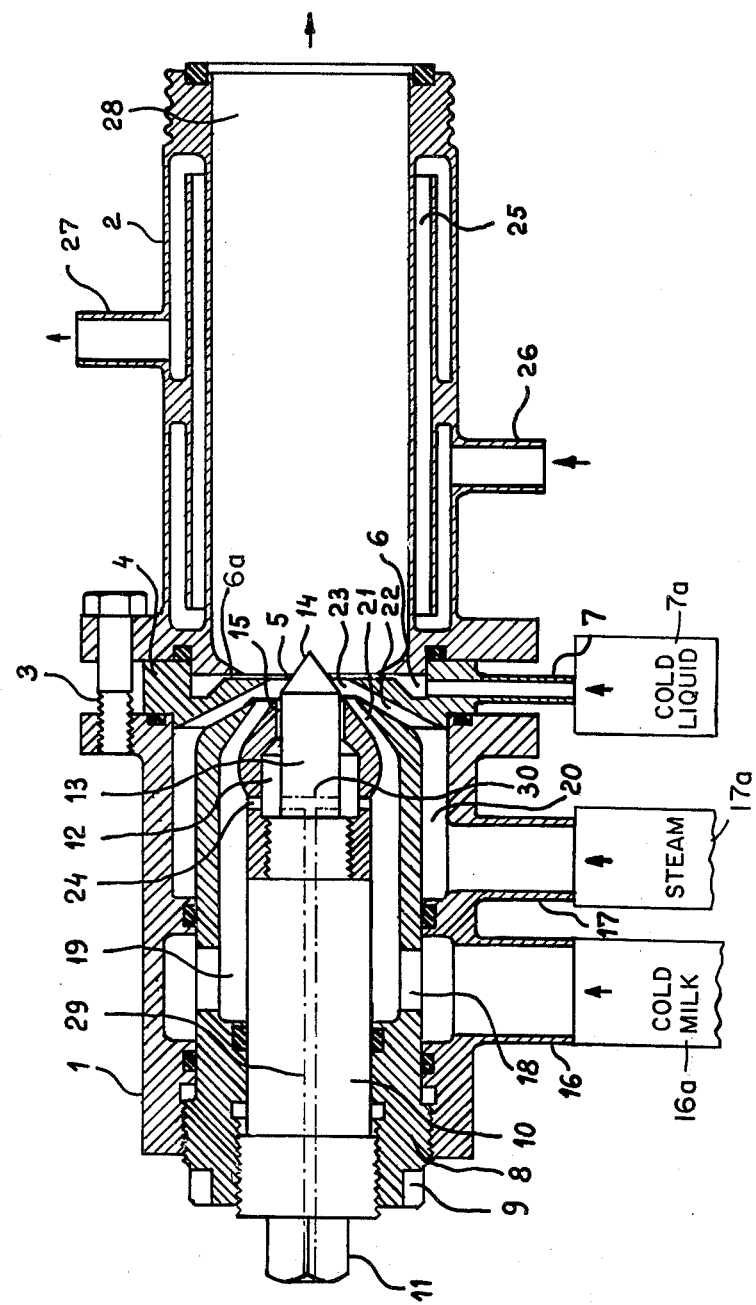

NOZZLE STERILIZER PROVIDING OUTER AND INNER ANNULAR CONCENTRIC COOLING JETS

The present invention relates to apparatus for sterilizing liquids, such as milk, blood or the like, by bringing annular jets of steam and liquid, concentric to each other, into contact with each other. The invention provides a jet nozzle for this purpose, the nozzle having annular, concentric channels for the supply of steam and liquid, which open around a central plug. An example of such a jet nozzle is shown in the U.S. Pat. No. 2,130,644.

This application is a division of our copending application Ser. No. 404,622 filed Oct. 9, 1973 and now U.S. Pat. No. 3,927,974.

Experience from plants for sterilizing liquid articles of food, such as milk, where the heating to the sterilization temperature (135° to 150° C) is effected by direct injection of steam into the liquid, shows that precipitation products, such as coagulated protein, coat surfaces of the jet nozzle. The coatings grow and cause the flow resistance in the nozzle to become so great that the pump and steam pressures are unable to overcome this resistance, which leads to interruption of the operation.

The present invention aims at preventing the formation of said coatings by providing means for flushing cold liquid past those surfaces on which the coatings can be formed. According to the invention, this is effected by providing two annular jets of cold liquid which are concentric to said jets of steam and liquid and which are caused to sweep along the formed annular jet of steam-heated liquid at its inside as well as at its outside. Preferably, the jets of cold liquid consist of the same liquid as that to be sterilized. However, it is also possible to use cold water or cold condensate of vapor emitted from the sterilized liquid.

A jet nozzle suitable for the new method is characterized in that the annular channels concentric to each other are four in number and that the innermost one and the outermost one of the channels are connected to a source of cold liquid. For constructional reasons, the simplest way to effect this is to connect the next innermost channel to the source for the liquid to be sterilized. For similar constructional reasons, it is suitable to arrange, within the housing of the jet nozzle, a connection between the channel for the liquid to be sterilized and at least one of the innermost and the outermost channels. In view of the tendency to precipitation of coagulated material on the surfaces of the jet nozzle, it has been found suitable to allow all channels to open mainly within a zone corresponding to a narrowing point of the central plug in the nozzle.

The invention is described more in detail below, reference being made to the accompanying DRAWING in which the single illustration is a longitudinal section through an example of the new jet nozzle.

The jet nozzle has a housing comprising two cylindrical parts 1 and 2. These parts are kept together by screws 3. A disc 4, clamped securely between these parts, has a central hole 5 into which opens an annular channel 6 for the supply of cold liquid from an inlet 7. A hollow cylindrical body 8 is screwed into the part 1, and its left-hand end has a grip 9 for a screwkey, which makes it possible to adjust the body 8 in relation to the disc 4. A cylindrical body 10 is in turn screwed into the body 8, and the relative position of the bodies 8 and 10 can be adjusted by means of a grip 11 for a screw-key. The latter grip is a part of the body 10. In its right-hand end, the body 10 has a cavity 12 into which a plug 13 with a conical point 14 is screwed. In passing through the right-hand end of the body 10, the plug 13 forms a narrow, annular slot 15 which, like the channel 6, has an unchangeable cross section. The body 1 has two inlets 16 and 17, of which the first one passes through an opening 18 in the body 8 and opens into the cavity 19 of the latter. The inlet 17 opens into the cavity 20 of the body 1. Conical, annular channels 21 and 22 lead from the cavities 19 and 20 to the meeting place 23 for the channels 6 and 15, i.e., to the zone of the plug point 14. The cavities 12 and 19 communicate with one another through holes 24.

Cooling channels 25 are arranged in the wall of the body 2, and these cooling channels have an inlet 26 and an outlet 27. Sterilized liquid discharges through an outlet 28. According to an alternative embodiment, the holes 24 can be plugged; and cold liquid can instead be supplied to the cavity 12 through an axial channel 29 in the body 10, which channel has radially extending branches 30.

The apparatus operates in the following manner, it being assumed that milk is to be sterilized. The milk is supplied from source 16a through the inlet 16 and the steam from source 17a through the inlet 17. Milk and steam meet in the zone 23 around the plug point 14, the milk immediately being heated to sterilizing temperature. A small part of the cold milk flows through the holes 24 to the slot 15 and sweeps from there along the plug point 14, so that precipitations on the latter are practically completely prevented. In a similar manner, cold milk coming from the inlet 7 prevents formation of precipitations on those surfaces of the jet nozzle which, calculated in the flow direction, follow after the opening 5, i.e., on the inside of the body 2. Cooling of this same inside by means of a supply of cold water through the inlet 26 assists in preventing formation of precipitations on this inside.

The width of the slots 21 and 22 can be adjusted by means of the key grips 9 and 11 so as to correspond to a suitable supply of milk and steam.

Cold water, such as cold condensate from milk vapor, can be supplied from source 7a to the inlet 7 instead of milk. The same is true for the channel 29, if the holes 24 have been plugged. On the lastmentioned condition, steam can be supplied through the inlet 16 and the milk to be sterilized can be supplied through the inlet 17.

As previously described, the channel 6 is an annular channel which receives cold liquid from inlet 7 and which opens into the central hole 5 in the disc 4. More precisely, the outlet 6a of annular channel 6 surrounds central plug 13 and the annular jet of steam-heated liquid issuing from the central hole 5, as shown in the drawing, so that the liquid from inlet 7 is directed along the outside of this annular jet issuing from hole 5.

We claim:

1. Apparatus for sterilizing a liquid such as milk, blood or the like, which comprises a jet nozzle having body means forming four annular concentric channels, namely, an innermost channel, an outermost channel and two intermediate channels intermediate said innermost and outermost channels, a central plug around the outside of which said four channels open, whereby said channel openings surround the central plug a source of steam and a source of liquid to be sterilized connected, respectively, to the two intermediate channels, and means for supplying cold liquid to said innermost and outermost channels.

2. The apparatus of claim 1, in which said source of liquid to be sterilized is connected to the intermediate channel next to said innermost channel.

3. The apparatus of claim 1, in which the channel connected to the source of liquid to be sterilized communicates with at least one of said innermost and outermost channels at a region upstream from where the four channels open around the central plug.

4. The apparatus of claim 1, in which the central plug has a tapered portion around which said four channels open.

* * * * *